United States Patent
Rupp et al.

(10) Patent No.: US 9,763,690 B2
(45) Date of Patent: Sep. 19, 2017

(54) SURGICAL INSTRUMENT WITH TRANSDUCER CARRIER ASSEMBLY

(75) Inventors: Kip M. Rupp, New Richmond, OH (US); Sora Rhee, Cincinnati, OH (US); Samantha L. Sheets, West Chester, OH (US); Daniel J. Mumaw, Johannesburg (ZA); Craig T. Davis, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 791 days.

(21) Appl. No.: 13/269,875

(22) Filed: Oct. 10, 2011

(65) Prior Publication Data

US 2013/0090575 A1 Apr. 11, 2013

(51) Int. Cl.
| | | |
|---|---|---|
| *A61B 8/00* | (2006.01) | |
| *A61B 17/32* | (2006.01) | |
| *A61B 17/29* | (2006.01) | |

(52) U.S. Cl.
CPC .............. *A61B 17/320092* (2013.01); *A61B 2017/2929* (2013.01)

(58) Field of Classification Search
CPC ........ A61B 17/3207; A61B 17/320092; A61B 2017/2929; A61B 7/3207; H04N 13/0406; H04N 13/0468; G11C 29/76
See application file for complete search history.

(56) References Cited

U.S. PATENT DOCUMENTS

| | | | |
|---|---|---|---|
| 5,322,055 A | 6/1994 | Davison et al. | |
| 5,361,768 A * | 11/1994 | Webler et al. | 600/445 |
| 5,938,633 A | 8/1999 | Beaupre | |
| 5,980,510 A | 11/1999 | Tsonton et al. | |
| 6,500,176 B1 | 12/2002 | Truckai et al. | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |

(Continued)

FOREIGN PATENT DOCUMENTS

| | | |
|---|---|---|
| CN | 1732861 A | 2/2006 |
| CN | 101495050 A | 7/2009 |

(Continued)

OTHER PUBLICATIONS

Partial European Search Report for Application No. EP 12 18 8003 dated Jan. 8, 2013.

(Continued)

*Primary Examiner* — Joel Lamprecht
(74) *Attorney, Agent, or Firm* — Frost Brown Todd LLC

(57) ABSTRACT

A surgical instrument includes an ultrasonic transducer, a body, and a transducer carrier assembly. The ultrasonic transducer is operable to deliver energy through the surgical instrument to a surgical site. The body is operable to house the ultrasonic transducer. The transducer carrier assembly is in communication with the body and the ultrasonic transducer. The transducer carrier assembly is operable to enable the translation and/or the rotation of the ultrasonic transducer within the body.

16 Claims, 10 Drawing Sheets

(56) References Cited

U.S. PATENT DOCUMENTS

| | | | |
|---|---|---|---|
| 7,354,440 B2 | 4/2008 | Truckal et al. | |
| 7,381,209 B2 | 6/2008 | Truckai et al. | |
| 7,416,101 B2 | 8/2008 | Shelton, IV et al. | |
| 7,738,971 B2 | 6/2010 | Swayze et al. | |
| 8,142,461 B2 | 3/2012 | Houser et al. | |
| 8,531,064 B2 | 9/2013 | Robertson et al. | |
| 2001/0037073 A1* | 11/2001 | White | A61B 8/12 600/585 |
| 2002/0151767 A1* | 10/2002 | Sonnenschein | A61B 1/0005 600/117 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0030311 A1* | 1/2009 | Stulen | A61B 17/320092 600/439 |
| 2009/0105597 A1* | 4/2009 | Abraham | A61B 8/08 600/466 |
| 2009/0143797 A1 | 6/2009 | Smith et al. | |
| 2009/0209979 A1 | 8/2009 | Yates et al. | |
| 2009/0209990 A1 | 8/2009 | Yates et al. | |
| 2009/0275864 A1* | 11/2009 | Hirai | 601/2 |
| 2010/0069940 A1 | 3/2010 | Miller et al. | |
| 2011/0015660 A1 | 1/2011 | Wiener et al. | |
| 2011/0087212 A1 | 4/2011 | Aldridge et al. | |
| 2011/0087218 A1 | 4/2011 | Boudreaux et al. | |
| 2012/0116379 A1 | 5/2012 | Yates et al. | |

FOREIGN PATENT DOCUMENTS

| | | |
|---|---|---|
| CN | 101548908 A | 10/2009 |
| CN | 101674781 A | 3/2010 |
| CN | 101765495 A | 6/2010 |
| CN | 102119005 A | 7/2011 |
| EP | 2 106 757 | 10/2009 |
| JP | H03-277359 A | 12/1991 |
| JP | 2011-189186 A | 9/2011 |
| WO | WO 2010/122288 A1 | 10/2010 |

OTHER PUBLICATIONS

Extended European Search Report date May 6, 2013 for Application No. EP 12188003.

Australian Office Action dated Jun. 7, 2016 for Application No. AU 2012232953, 4 pgs.

Chinese Office Action dated Oct. 30, 2015 for Application No. CN 201210397410.5, 21 pgs.

Japanese Office Action dated Jun. 21, 2016 for Application No. JP 2012-223856, 6 pgs.

* cited by examiner

SURGICAL INSTRUMENT WITH TRANSDUCER CARRIER ASSEMBLY

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004, the disclosure of which is incorporated by reference herein.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
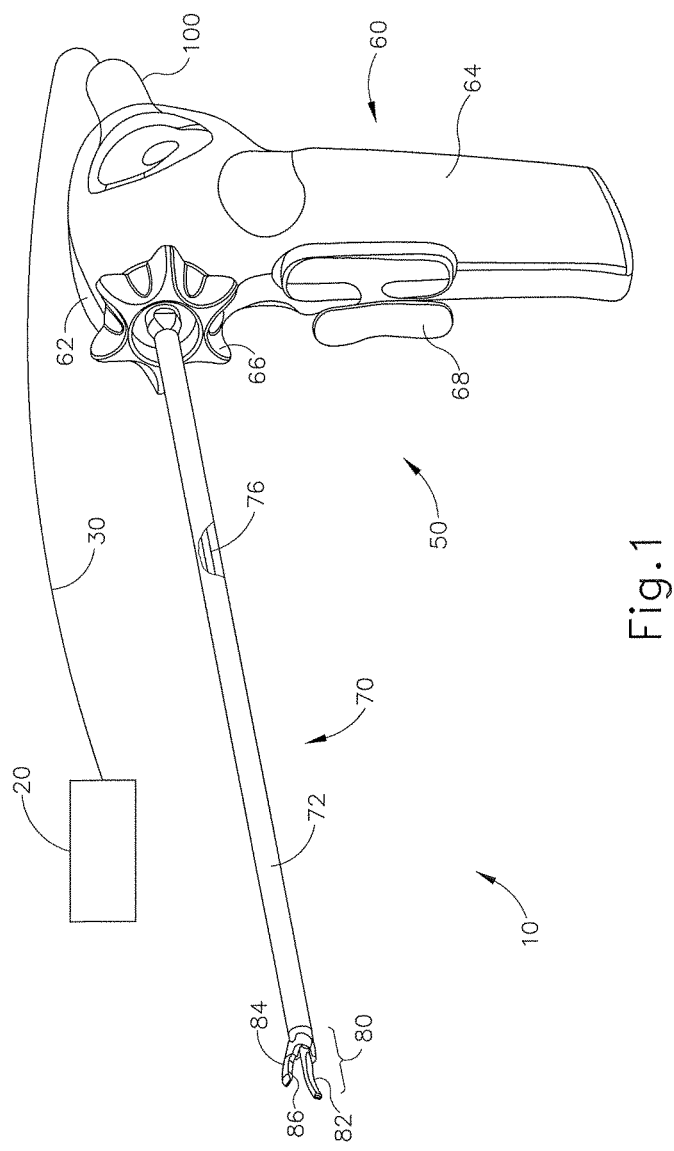
FIG. 1 depicts a perspective view of an exemplary surgical system having a surgical instrument and a generator.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

Various examples described herein are directed to improved ultrasonic surgical instruments configured for effecting tissue dissecting, cutting, and/or coagulation during surgical procedures. For example, the teachings herein may be readily combined with various teachings from any of the following, in numerous ways, as will be apparent to those of ordinary skill in the art: U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein; U.S. Pub. No. 2009/0209990 entitled "Motorized Surgical Cutting and Fastening Instrument Having Handle Based Power Source," published Aug. 20, 2009, now U.S. Pat. No. 8,657,172, issued on Feb. 25, 2014, the disclosure of which is incorporated by reference herein; U.S. Pub. No. 2010/0069940 entitled "Ultrasonic Device for Fingertip Control," published Mar. 18, 2010, now U.S. Pat. No. 8,657,172, issued on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

As will become apparent from the following description, it is contemplated that versions of the surgical instrument described herein may be used in association with an oscillator module of a surgical system, whereby ultrasonic energy from the oscillator module provides the desired ultrasonic actuation for the present surgical instrument. It is also contemplated that versions of the surgical instrument described herein may be used in association with a signal generator module of a surgical system, whereby electrical energy in the form of radio frequencies (RF), for example, is used to provide feedback to the user regarding the surgical instrument. The ultrasonic oscillator and/or the signal generator modules may be non-detachably integrated with the surgical instrument or may be provided as separate components, which can be electrically attachable to the surgical instrument.

It should also be understood that the teachings herein may be readily applied to various types of electrosurgical instruments, including but not limited to those taught in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, now U.S. Pat. No. 9,161,803, issued on Oct. 20, 2015, the disclosure of which is incorporated by reference herein.

Furthermore, the teachings herein may be readily applied to various types of electrically powered cutting and stapling instruments, including but not limited to those taught in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pub. No. 2009/0209979, entitled "Motorized Cutting and Fastening Instrument Having Control Circuit for Optimizing Battery Usage," published Aug. 20, 2009, now U.S. Pat. No. 8,622,274, issued on Jan. 7, 2014; and U.S. patent application Ser. No. 13/151,481, entitled "Motor Driven Electrosurgical Device with Mechanical and Electrical Feedback," filed Jun. 2, 2011, now U.S. Pat. No. 9,161,803, issued on Oct. 20, 2015, the disclosure of which is incorporated by reference herein. Still other suitable types of devices to which the teachings herein may be applied will be apparent to those of ordinary skill in the art.

In view of the foregoing, it should be understood that the surgical instrument is not limited in its application or use to the details of construction and arrangement of parts illustrated in the accompanying drawings and description. The illustrative versions of the surgical instrument may be implemented or incorporated in other versions, variations and modifications, and may be practiced or carried out in various ways. Further, unless otherwise indicated, the terms and expressions employed herein have been chosen for the purpose of describing the illustrative versions of the present surgical instrument for the convenience of the reader and are not for the purpose of limiting the surgical instrument.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Ultrasonic Surgical System

FIG. 1 shows an exemplary ultrasonic surgical system (10) comprising an ultrasonic surgical instrument (50), generator (20), and a cable (30) coupling generator (20) to surgical instrument (50). In the present example, a suitable generator (20) comprises the GEN 300 sold by Ethicon Endo-Surgery, Inc. of Cincinnati, Ohio, but any suitable generator (20) may be used as would be apparent to one of ordinary skill in the art in view of the teachings herein. By way of example only, generator (20) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. While surgical instrument (50) will be described in reference to an ultrasonic surgical instrument it should be understood that the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuating member (not shown), a waveguide (76), and an end effector (80) located on the distal end of transmission assembly (70). In the present example, end effector (80) comprises a blade (82) that is mechanically and acoustically coupled to the waveguide (76), a clamp arm (84) operable to pivot at the proximal end of transmission assembly (70), and, optionally a clamp pad (86) coupled to clamp arm (84). Clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein.

End effector (80) and transmission assembly (70) will be discussed in greater detail below in reference to the example shown in FIG. 4. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744, issued on Jun. 11, 2013; U.S. Pat. No. 6,500,176; U.S. Pat. Pub. No. 2011/0087218, now U.S. Pat. No. 8,939,974, issued on Jan. 27, 2015; and/or U.S. Pat. Pub. No. 2009/0143797, now U.S. Pat. No. 8,419,757, issued Apr. 16, 2013.

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Mating housing portion (62) will be discussed in greater detail below in reference to FIG. 2. Lower portion (64) of multi-piece handle assembly (60) shown in FIG. 1 includes a trigger (68) and is configured to be grasped by a user using a single hand. One merely exemplary alternative configuration for lower portion (64) is depicted in FIG. 1 of U.S. Pat. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein. Toggle buttons (69), shown in FIG. 2 of the present disclosure, are located on a distal surface of lower portion (64) and are operable to activate transducer (100) at different operational levels using generator (20). For instance, a first toggle button (69) may activate transducer (100) at a maximum energy level while a second toggle button (69) may activate transducer (100) at a minimum, non-zero energy level. Of course, toggle buttons (69) may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). The trigger portion is operable to activate transducer (100) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744issued on Jun. 11, 2013; U.S. Pat. No. 6,500,176; U.S. Pat. Pub. No. 2011/0087218, now U.S. Pat. No. 8,939,974, issued on Jan. 27, 2015; and/or U.S. Pat. Pub. No. 2009/0143797, now U.S. Pat. No. 8,419,757, issued Apr. 16, 2013.

II. Exemplary Coupling Assemblies for Ultrasonic Surgical Instrument

In some instances it may be useful to detach transmission assembly (70) from multi-piece handle assembly (60) and transducer (100). For instance, a detachable transmission assembly (70) may permit the reuse of multi-piece handle assembly (60) with multiple transmission assemblies (70) having various end effectors (80). By way of example only, the various end effectors (80) may have different sized and/or shaped blades (82) or the various end effectors (80) may have entirely different functions, such as RF end effectors, stapling end effectors, cutting end effectors, etc. Furthermore, a single multi-piece handle assembly (60) may be reused for different operations by a user by removing a dirty transmission assembly (70), optionally cleaning multi-piece handle assembly (60), and coupling a new transmission assembly (70) to multi-piece handle assembly (60) for a new operation. Accordingly, configuring multi-piece handle assembly (60) to couple to a variety of transmission assemblies (70) may be preferable for some users of surgical instrument (50).

A. Exemplary Multi-Piece Handle Assembly

Figure 2:
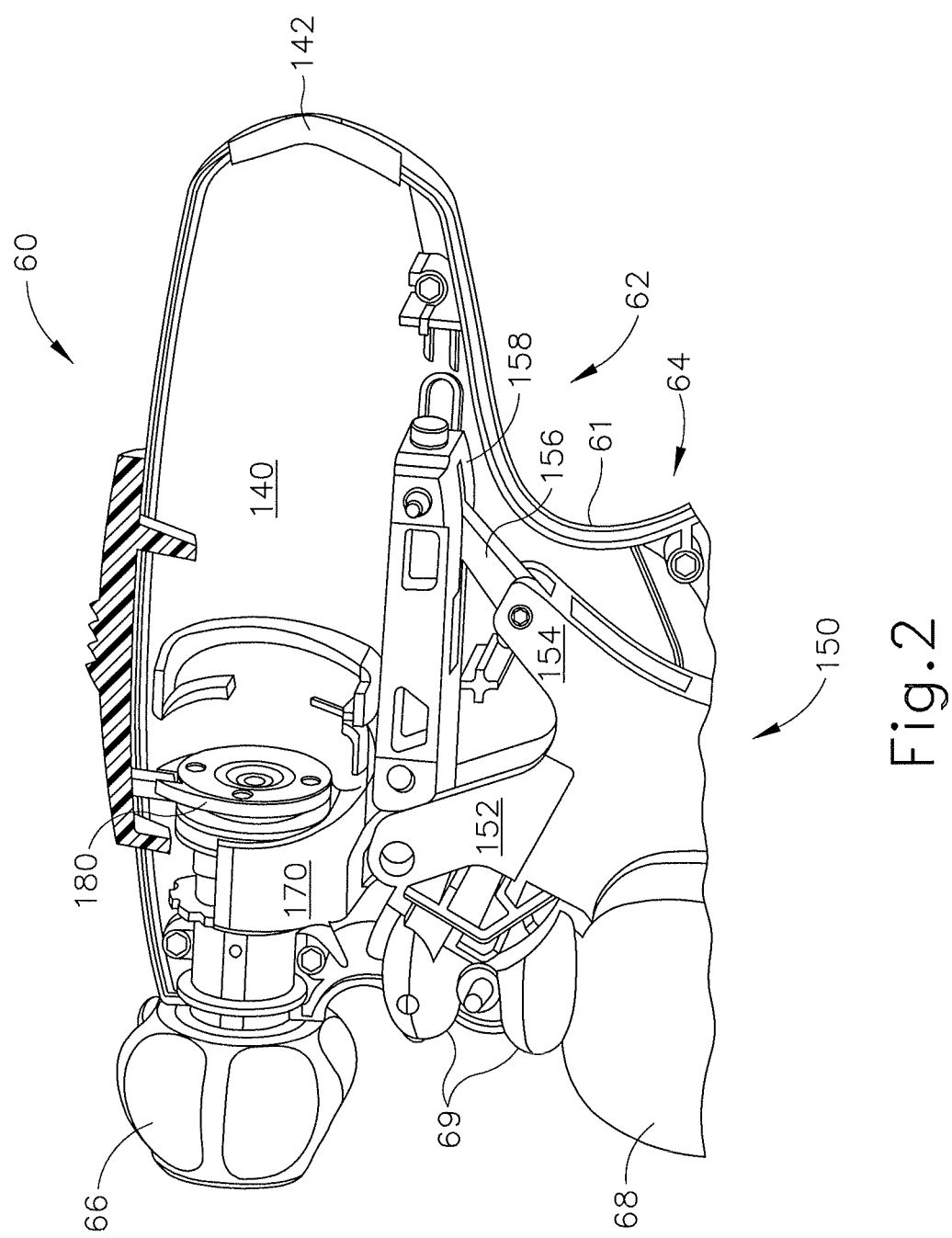
FIG. 2 depicts a partial side elevation view of an exemplary surgical instrument with a portion of a cover removed to show the interior of a mating housing portion of an exemplary multi-piece handle assembly.

FIG. 2 shows a partial side view of multi-piece handle assembly (60) with a portion of a cover (61) removed to show the internal components contained within mating housing portion (62) and a section of lower portion (64). As described above, lower portion (64) includes a pivotable trigger (68) and a pair of toggle buttons (69). Trigger (68) of the present example is pivotable from a distal, open position to a proximal, closed position. A trigger assembly (150) is coupled to trigger (68) and is pivotally supported within multi-piece handle assembly (60). Trigger assembly (150) of the present example comprises a pivotable attachment arm (152) that may be pivoted about a pin (not shown), a trigger arm (154), an intermediate link (156), and an actuation arm (158). Actuation arm (158) is coupled to a trigger yoke (170) at the distal end of actuation arm (158). Actuation arm (158) comprises one or more mounting pins (not shown) extending outwardly from actuation arm (158). The mounting pins are sized to be slidably received in a corresponding elongated channel formed in cover (61). Accordingly, when trigger (68) is pivoted proximally from the open position to the closed position, attachment arm (152) and trigger arm (154) pivot within multi-piece handle assembly (60). Intermediate link (156) coupled to trigger arm (154) transfers this pivoting motion from trigger arm (154) to actuation arm (158) to slidably translate actuation arm (158) proximally via mounting pins within the elongated channel. Trigger yoke (170), which is coupled to actuation arm (158), is translated proximally as well. In one configuration, trigger yoke (170) is coupled to a force-limiting mechanism (180) that is coupled to transmission assembly (70), as will be described in more detail below, to operate an inner tubular actuating member. A cavity (140), shown in FIG. 2, is configured to receive transducer (100) therein from a transducer aperture (142) formed in cover (61). Cavity (140) is configured to receive at least a portion of transducer (100) therein such that transducer (100) and transmission assembly (70) may be coupled together. Still other configurations for multi-piece handle assembly (60) will be apparent to one of ordinary skill in the art in view of the teachings herein.

B. Exemplary Transducer

Figure 3:
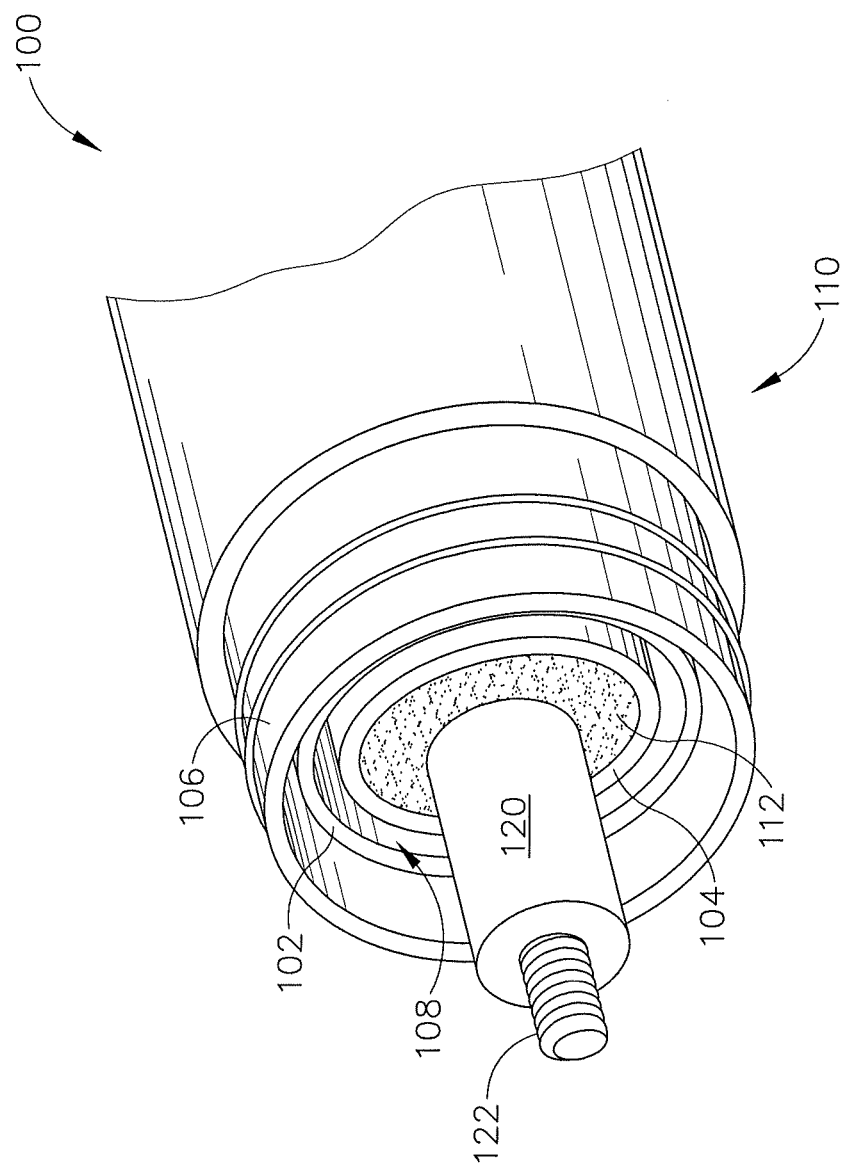
FIG. 3 depicts a partial perspective view of a distal end of an exemplary transducer.

As shown in FIG. 3, transducer (100) of the present example is a tubular component that is coupled to generator (20) via cable (30), though it should be understood that transducer (100) may be a cordless transducer. For instance, transducer (100) may receive power from a power source that is contained within handle assembly (60), in accordance with the teachings of various references cited herein or otherwise. In the present example, transducer (100) includes a first conductive ring (102) and a second conductive ring (104) which are disposed within a body (110) of transducer (100). In one configuration, first conductive ring (102) comprises a ring member that is disposed between body (110) and a horn (120) extending distally from body (110). Horn (120) comprises distal horn threads (122) such that horn (120) is coupleable to waveguide (210), as will be discussed below in reference to FIG. 4. First conductive ring (102) is formed adjacent to, or as part of a flange (106) within a transducer cavity (108) such that first conductive ring (102) is electrically isolated from second conductive ring (104) and other conductive components of transducer (100). First conductive ring (102) is located on a non-conductive platform extending distally from body (110). First conductive ring (102) is electrically coupled to cable (30), shown in FIG. 1, by one or more electrical wires or conductive etchings (not shown) within body (110).

Second conductive ring (104) of transducer (100) similarly comprises a ring member that is disposed between body (110) and horn (120). Second conductive ring (104) is disposed between first conductive ring (102) and horn (120). As is shown in FIG. 3, first and second conductive rings (102, 104) are coaxial members. Second conductive ring (104) is likewise electrically isolated from first conductive ring (104) and other conductive components of transducer (100). Similar to first conductive ring (102), second conductive ring (104) extends from the non-conductive platform. One or more washer-shaped spacers (112) may be disposed between second conductive ring (104) and horn (120) to isolate the vibrations from horn (120) from the other components of transducer (100). Second conductive ring (104) is also electrically coupled to cable (30), shown in FIG. 1, one or more electrical wires or conductive etchings (not shown) within body (110). As will be described in greater detail below, the coupling between second conductive ring (104) and cable (30) may permit transducer (100)

to rotate and/or translate relative to cable (30). One merely exemplary suitable ultrasonic transducer (100) is Model No. HP054, sold by Ethicon Endo-Surgery, Inc. of Cincinnati, Ohio, though it will be understood that any other suitable transducer may be used.

As shown in the present example, the distal end of transducer (100) threadably couples to the proximal end of transmission assembly (70) via horn (120). The distal end of transducer (100) also interfaces with one or more electrical connections (not shown) via first and second conductive rings (102, 104) to electrically couple transducer (100) to toggle buttons (69) to provide a user with finger-activated controls for activating transducer (100) while using surgical instrument (50). Still other configurations for transducer (100) will be apparent to one of ordinary skill in the art in view of the teachings herein. For instance, first and second conductive rings (102, 104) may be omitted from the distal end of transducer (100) and the electrical coupling of transducer (100) to toggle buttons (69) may be accomplished by alternative methods, such as conductors at the proximal end of transducer (100), conductors located along the side of body (110) of transducer (100), directly from cable (30) and/or any other method as will be apparent to one of ordinary skill in the art in view of the teachings herein. When transducer (100) of the present example is activated via a toggle button (69), transducer (100) is operable to create mechanical energy in the form of linear oscillations or vibrations (e.g. torsional or transverse), at an ultrasonic frequency (such as 55.5 kHz). If transducer (100) is coupled to transmission assembly (70) via horn (120), then these mechanical oscillations are transmitted through waveguide (76) to end effector (80). In the present example, blade (82), being coupled to waveguide (76), oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to cauterize the tissue. While some configurations for transducer (100) have been described, still other suitable configurations for transmission assembly (70) and transducer (100) will be apparent to one of ordinary skill in the art in view of the teachings herein.

C. Exemplary Transmission Assembly for Threaded Attachment

As noted previously, in some instances it may be useful to detach transmission assembly (70) from multi-piece handle assembly (60) and transducer (100). Merely exemplary instances include the use of multi-piece handle assembly (60) with multiple transmission assemblies (70) having different sized and/or shaped blades (82), use with various end effectors (80) with entirely different functions and/or modalities (e.g., RF end effectors, stapling end effectors, cutting end effectors, and/or etc.), or for reuse of a single multi-piece handle assembly (60) for multiple operations by a user. Accordingly, a configuration permitting the user to swap transmission assemblies (70) with multi-piece handle assembly (60) may be useful.

Figure 4:
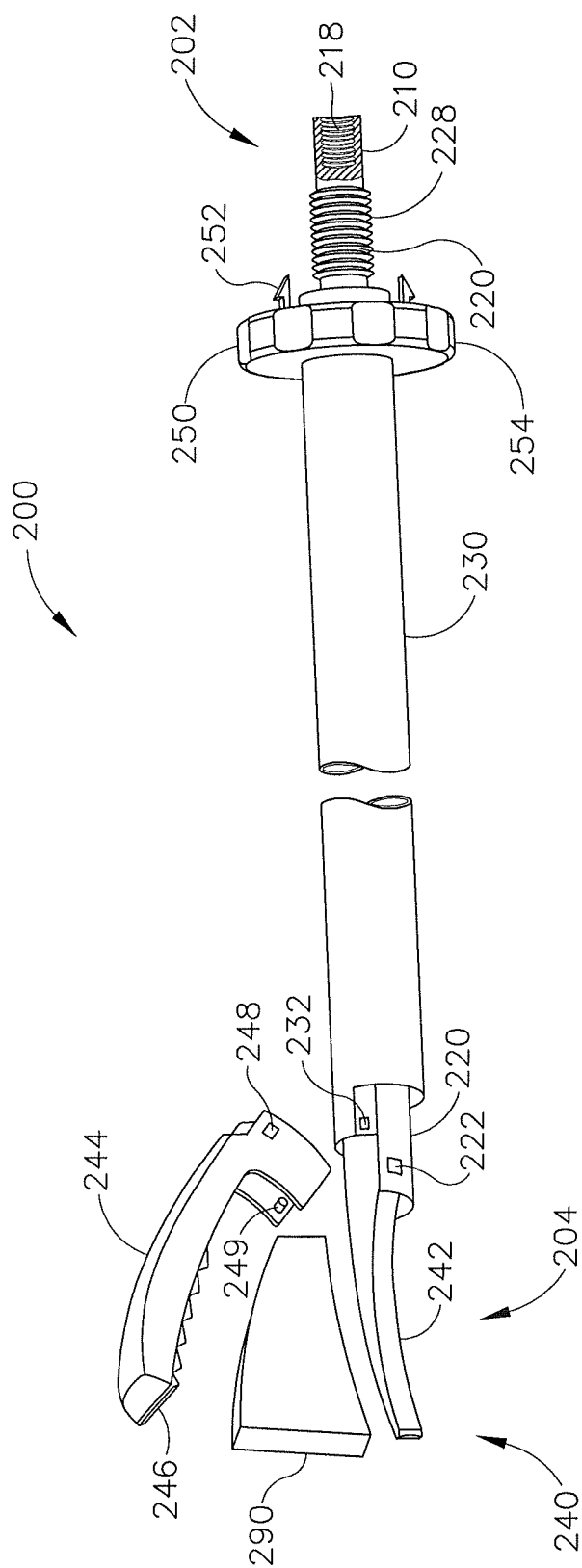
FIG. 4 depicts a perspective view of an exemplary transmission assembly.

One merely exemplary transmission assembly (200) is shown in FIG. 4 having a proximal end (202), a distal end (204), a wave guide (210), an inner tubular actuating member (220), an outer sheath (230), and an end effector (240) at the distal end of transmission assembly (200). In the present example, waveguide (210), inner tubular actuating member (220), and outer sheath (230) are coaxial members with waveguide (210) in the center, inner actuating member (220) disposed about waveguide (210), and outer sheath (230) disposed about inner actuating member (220).

Referring to distal end (204) of transmission assembly (200) first, end effector (240) comprises a blade (242), a clamp arm (244), and one or more optional clamp pads (246). In the present example, blade (242) is coupled to waveguide (210) such that the mechanical vibrations transmitted to waveguide (210) from transducer (100) are also transmitted to blade (242). Merely exemplary couplings for blade (242) to waveguide (210) include welding blade (242) to waveguide (210), integrally forming blade (242) with waveguide (210), mechanically or chemically coupling blade (242) to waveguide (210), and/or any other suitable configuration as will be apparent to one of ordinary skill in the art in view of the teachings herein. In some versions, blade (242) is a curved blade, such as blade (242) shown in FIG. 4; and in some versions, blade (242) may be a straight blade. Furthermore, blade (242) may have a variety of shapes and sizes. In the present example, blade (242) is a tapered rectangular blade, though it should be understood that blade (242) may include cylindrical, triangular, hemi-cylindrical, square, hooked, and/or any other shape for blade (242). Furthermore, additional features may be added to blade (242), including spherical tips, hooked tips, square tips, serrated edging, and/or any other additional features. Still other configurations for blade (242) will be apparent to those of ordinary skill in the art in view of the teachings herein.

Clamp arm (244) of the present example is a curved member that corresponds to the curvature of blade (242). Clamp arm (244) may optionally include clamp pads (246) to grip or secure tissue against blade (242). Such clamp pads may be configured in accordance with at least some of the teachings of U.S. Pat. Pub. No. 2006/0079874, entitled "Tissue Pad Use with an Ultrasonic Surgical Instrument," published Apr. 13, 2006, the disclosure of which is incorporated by reference herein. Pivotal movement of clamp arm (244) with respect to blade (242) is accomplished by a first pair of pivot points (248) on clamp arm (244) that pivotally couple to outer sheath (230) and a second set of pivot points (249) on clamp arm (244) that pivotally couple to inner tubular actuating member (220). In one merely exemplary configuration, outer sheath (230) is coupleable to multi-piece handle assembly (60) through a rotation knob (250), as will be described in greater detail below. First set of pivot points (248) of clamp arm (244) are pivotally connected to outer sheath (230) via corresponding through holes (232) on outer sheath (230). In one configuration, first set of pivot points (248) comprise through holes and a securing pin or rivet may be inserted through first set of pivot points (248) and through through holes (232) to secure clamp arm (244) to outer sheath (230). The pin in this configuration may be laser welded to clamp arm (244) or the pin may be laser welded to outer sheath (230). Of course through holes (232) may instead be outwardly extending pins and first set of pivot points (248) may be through holes. Still other configurations for first set of pivot points (248) and through holes (232) will be apparent to one of ordinary skill in the art in view of the teachings herein.

Second set of pivot points (249) of clamp arm (244) are pivotally connected to inner tubular actuating member (220) via corresponding through holes (222) on inner tubular actuating member (220). In one configuration, second set of pivot points (249) comprise through holes and a securing pin or rivet may be inserted through second set of pivot points (249) and through through holes (222) to secure clamp arm (244) to inner tubular actuating member (220). The pin in this configuration may be laser welded to clamp arm (244) or the pin may be laser welded to inner tubular actuating member (220). Of course through holes (222) may instead be outwardly extending pins and second set of pivot points (249) may be through holes. Still other pivotable configurations for second set of pivot points (249) and through holes (222) will be apparent to one of ordinary skill it the art in view of the teachings herein.

With clamp arm (244) so secured to outer sheath (230) and inner tubular actuating member (220), clamp arm (244) is pivotable when inner tubular actuating member (220) translates longitudinally. In the present configuration, inner tubular actuating member (220) is translatable relative to the longitudinal axis of outer sheath (230) and is coupled to force-limiting mechanism (180) within multi-piece handle assembly (60). Thus, when force-limiting mechanism (180) translates via trigger (68) and trigger assembly (150), clamp arm (244) is pivotable from an open position to a closed position. This may permit a user to couple transmission assembly (200) to multi-piece handle assembly (60) while maintaining both clamp arm (244) and trigger (68) in their respective open positions. Alternatively, a user may couple transmission assembly (200) to multi-piece handle assembly (60) without the use of a spacer (290). For example, the user may couple different components of transmission assembly (200) with different components of handle assembly (60) at different times, such as in the manner described below or otherwise.

Referring now to proximal end (202) of transmission assembly (200), a rotation knob (250) couples outer sheath (230) to multi-piece handle assembly (60). In the present example, rotation knob (250) comprises an inner ring portion (not shown) having one or more connectors (252) extending proximally therefrom, an outer ring (254), and a pin (not shown) extending through outer ring (254), outer sheath (230), inner tubular actuating member (220), and waveguide (210). Accordingly, when outer ring (254) of rotation knob (250) is rotated, waveguide (210), inner tubular actuating member (220), and outer sheath (230) also rotate. Inner ring portion and outer ring (254) of the present example are complementary bearing components such that outer ring (254) is rotatable relative to inner ring portion. It should be understood that the pin does not extend though inner ring portion. As previously noted, inner ring portion includes connectors (252). In the present example connectors (252) are shown as snap-fit connectors, though other suitable connecting features, such as threading, adhesives, pins, clips, snaps, and/or other connectors may be used as will be apparent to one of ordinary skill in the art in view of the teachings herein. When transmission assembly (200) is assembled with multi-piece handle assembly (60) and transducer (100), as will be discussed below, connectors (252) of the present example insert into one or more recesses (not shown) and couple rotation knob (250) to cover (61) of multi-piece handle assembly (60). A release mechanism, such as a push button (not shown) on multi-piece handle assembly (60) or on rotation knob (250) may be provided to decouple connectors (252) from cover (61) when transmission assembly (200) is to be removed. Alternatively, connectors (252) may be designed to break-away when transmission assembly (200) is decoupled. Further still, if threading is used, inner portion of rotation knob (250) may be rotated to decouple from multi-piece handle assembly (60). Still other suitable configurations for rotation knob (250) will be apparent to one of ordinary skill in the art in view of the teachings herein.

Still referring to proximal end (202) of transmission assembly (200), external threads (228) are included at the proximal end of inner tubular actuating member (220) as shown in FIG. 4. External threads (228) screw into complementary threads (not shown) of force limiting mechanism (180), which is in turn driven by trigger assembly (150). Additionally, a recess having internal threading (218) is included at the proximal end of waveguide (210) as shown in FIG. 4. Internal threading (218) screws onto horn threads (122) to couple waveguide (210) to transducer (100). Of course other suitable configurations for transmission assembly (200) will be apparent to one or ordinary skill in the art in view of the teachings herein. Similarly, various suitable ways in which transmission assembly (200) may be coupled with handle assembly (60) will be apparent to those of ordinary skill in the art in view of the teachings herein.

III. Exemplary Surgical Instrument Transducer Carrier Assembly

It will be appreciated that in some instances during the course of use, it may be desirable to move transducer (100) in a variety of ways relative to handle assembly (60). For instance, transducer (100) may be rotated and/or translated. The components and arrangement described below enable rotation and translation of transducer (100) relative to handle assembly (60). By way of example only, a user may wish to rotate transducer (100) relative to handle assembly (60) to more conveniently orient end effector (80, 240). A user may wish to translate transducer (100) relative to handle assembly (60) to change the effective length of transmission assembly (70, 200). In some versions, this may optimize use of a shortened transmission assembly (70, 200) for open surgical procedures and a lengthened transmission assembly (70, 200) for minimally invasive laparoscopic procedures performed through a trocar, etc. In addition or in the alternative, regardless of the type of procedure, a user may wish to adjust the effective length of transmission assembly (70, 200) to achieve a desired balance of reach, control, and/or other use characteristics. Examples of uses for changing the longitudinal position of a harmonic blade relative to a handle assembly are described in U.S. Pub. No. 2008/0200940, the disclosure of which is incorporated by reference herein.

Figure 5:
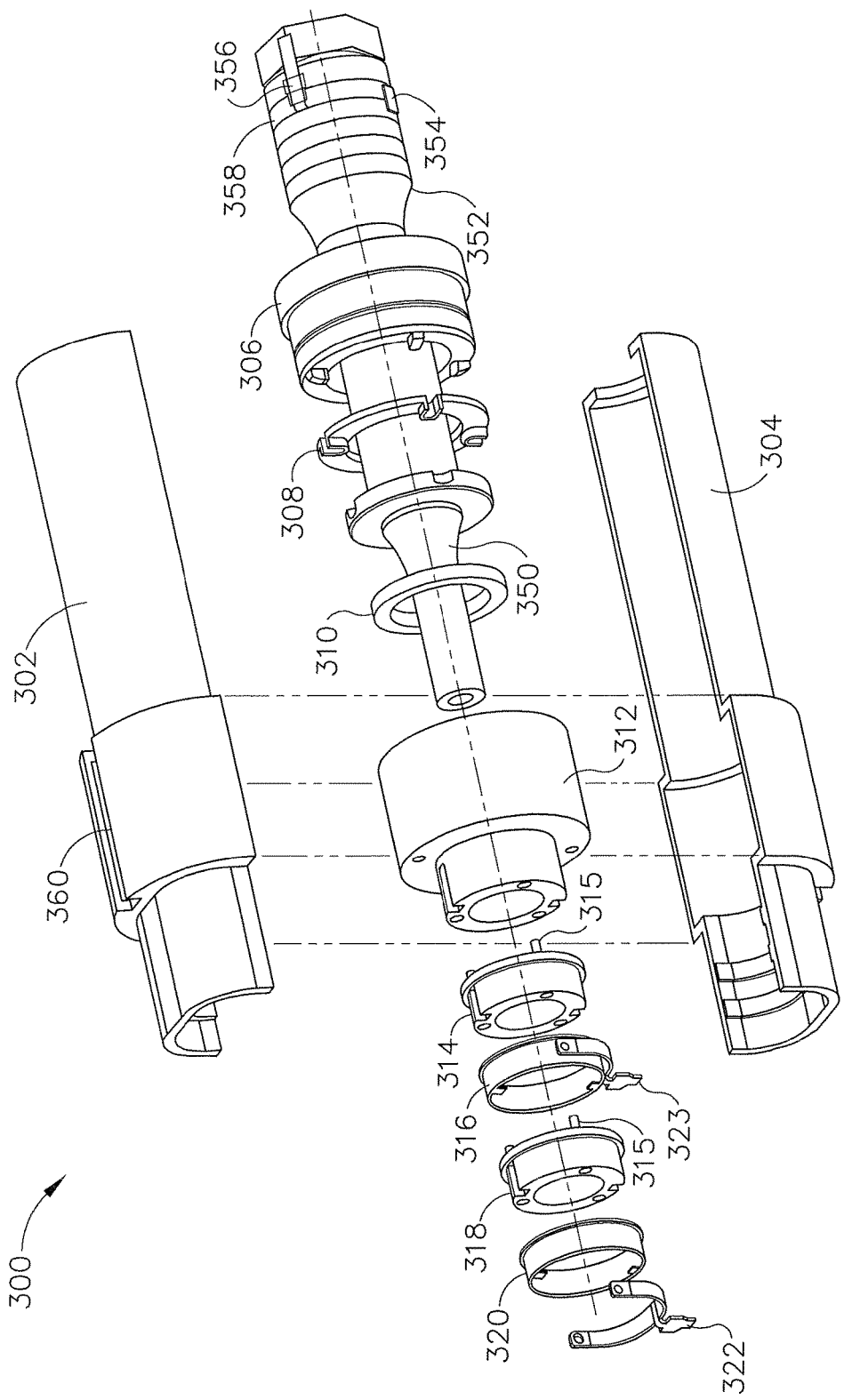
FIG. 5 depicts a perspective, exploded view of an exemplary transducer carrier assembly.

FIG. 5 shows an exemplary transducer carrier assembly (300). Transducer carrier assembly (300) comprises a first cover (302) and a second cover (304). First cover (302) and second cover (304) are symmetrically shaped and are operable to mechanically couple with each other. In the present example, first cover (302) is positioned above second cover (304), but it will be appreciated that any suitable orientation for first cover (302) and second cover (304) may be used as would be apparent to one of ordinary skill in the art in view of the teachings herein. When coupled, first cover (302) and second cover (304) form a generally cylindrical shape defining a hollow cavity extending through first cover (302) and second cover (304). In the present example, the interior of first cover (302) and second cover (304) are contoured to complement an object placed within first cover (302) and second cover (304). However, first cover (302) and second cover (304) may have any suitable shape as would be apparent to one of ordinary skill in the art in view of the teachings herein. Furthermore, first cover (302) comprises a keyway (360) operable to mechanically engage a key formed in the body of, for example, handle assembly (60) (shown in FIG. 1). Second cover (304) comprises an analogous keyway (not shown) operable to engage an analogous key formed in the body of handle assembly (60). As a result of the handle assembly (60) key engaging keyway (360), first cover (302) and second cover (304) are operable to translate within handle assembly (60). A transducer (352), which will be described in more detail below, is operable to rotate within first cover (302) and second cover (304).

Transducer carrier assembly (300) comprises a mid housing (306) and a keyed ring (308) shaped to fit mid housing (306). Keyed ring (308) is operable to provide acoustic isolation between transducer (351) and mid housing (306). Furthermore, an o-ring (310) is also in communication with mid housing (306). While in the present example, o-ring (310) is positioned distally in relation to keyed ring (308), it will be appreciated that any suitable configuration may be used as would be apparent to one of ordinary skill in the art in view of the teachings herein. For example, o-ring (310) and mid housing (306) may be integrally formed or may be constructed as separate components as shown in the illustrated version. A transducer (352) extends through the center of transducer carrier assembly (300). A horn (350) sits at the distal end of transducer (352) and is operable to communicate with an end effector (80) (shown, for example, in FIG. 1) via a waveguide to deliver energy (ultrasonic vibrations) to a surgical site. The proximal end of transducer (352) comprises a stack of piezo elements (358). A first lead (354) and a second lead (356) are positioned on the outside of piezo elements (358) and may be activated with electrical power to cause piezo elements (358) to vibrate at ultrasonic frequencies.

Figure 7:
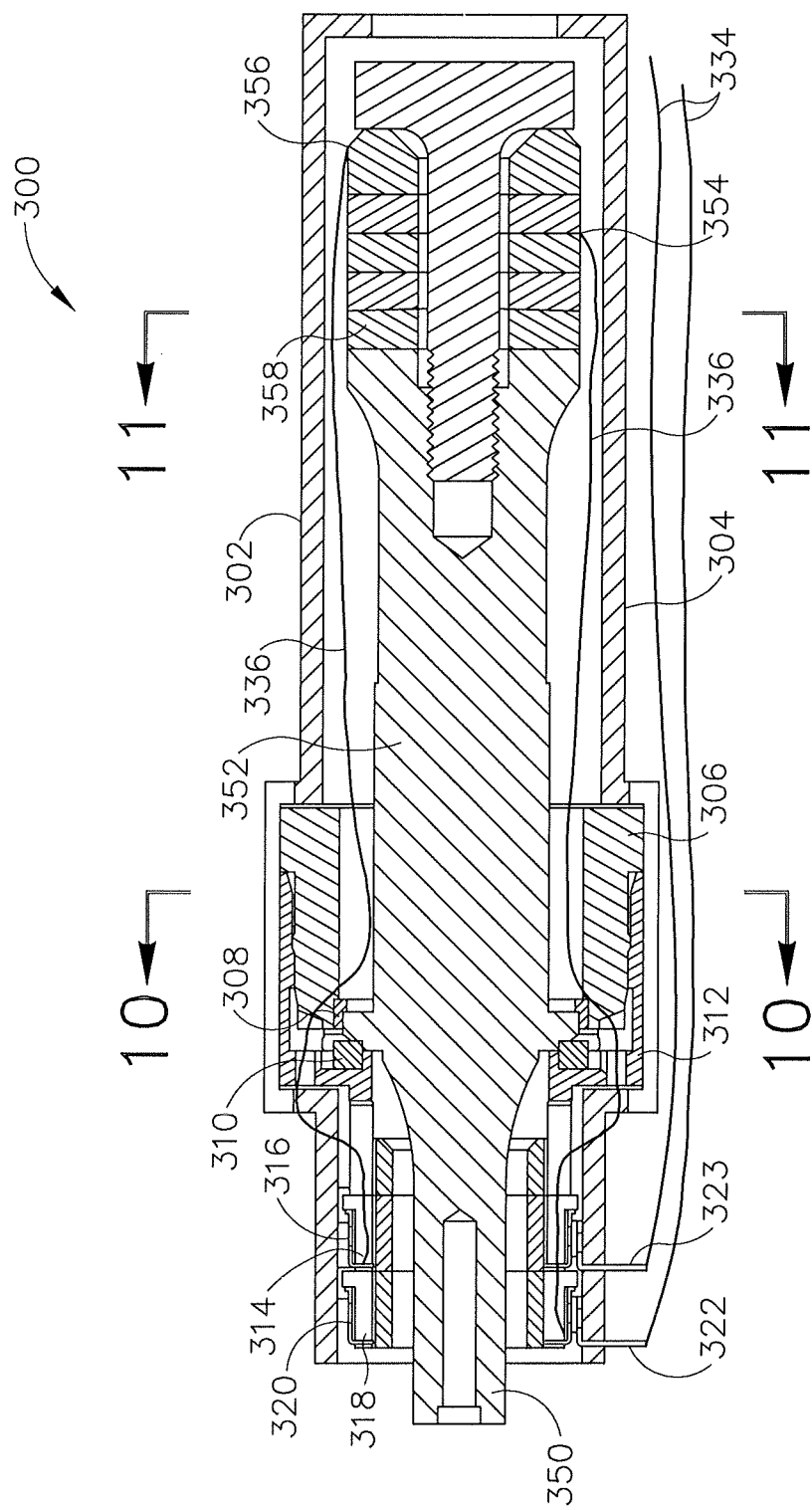
FIG. 7 depicts a side cross sectional view of the transducer carrier assembly of FIG. 5.

Transducer carrier assembly (300) further comprises a nose cone (312), a first drum housing (314), a first drum contact (316), a second drum housing (318), and a second drum contact (320). As best seen in FIG. 7, mid housing (306) is inserted into the proximal end of nose cone (312). A first housing contact (323) is coupled to first drum contact (316), and a second housing contact (322) is coupled to second drum contact (320). First housing contact (323) comprises a downwardly extending tab connected to a half-ring, which forms a slip-ring contact resiliently biased to contact first drum contact (316). First drum contact (316) may rotate while first housing contact (323) remains rotationally fixed. As a result, first housing contact (323) and first drum contact (316) are operable to maintain electrical continuity while first drum contact (316) rotates relative to first housing contact (323). Second housing contact (322) also comprises a downwardly extending tab connected to a half-ring, which forms a slip-ring contact resiliently biased to contact second drum contact (320). Second drum contact (320) may rotate while second housing contact (322) remains rotationally fixed. Second housing contact (322) and second drum housing (320) are also operable to maintain electrical continuity while second drum contact (320) rotates relative to second housing contact (322). As a result, any wires, etc. connected to housing contacts (323, 322) may be in electrical communication with drum contacts (316, 320), respectively, as will be described in further detail below.

First drum contact (316) encircles first drum housing (314) such that first drum housing (314) may rotate together with first drum contact (316). Thus, first drum contact (316) and first drum housing (314) may both rotate according to movement of transducer carrier assembly (300) caused by the user, or through normal operation of transducer (100). Second drum contact (320) and second drum housing (318) may have a similar construction to first drum contact (316) and first drum housing (314) such that second drum contact (320) may rotate together with second drum housing (318).

First drum housing (314) is operable to couple with nose cone (312). In particular, first drum housing (314) comprises at least one proximally extending post (315) able to couple with at least one post hole (326) of nose cone (312), which can be seen more clearly in FIG. 6. In the exemplary version, first drum housing (314) has three posts (315) spaced apart equally around the proximal face of first drum housing (314). Furthermore, nose cone (312) has a number of post holes (326) equal to the number of posts (315). However, it will be appreciated that any suitable number of posts (315) and post holes (326) may be used as would be apparent to one of ordinary skill in the art in view of the teachings herein. For example, 2, 3, 4, 5, 6, etc. number of posts (315) and/or post holes (326) may be used. Additionally, posts (315) and post holes (326) need not necessarily be equal in number. While the illustrated version comprises posts (315) and post holes (326) for coupling first drum housing (314) and nose cone (312), it will be appreciated that other coupling features may be used as would be apparent to one of ordinary skill in the art in view of the teachings herein. For example, snap clips, screws, or any other suitable coupling mechanism may be used. Once coupled, as nose cone (312) rotates or translates, first drum housing (314) analogously rotates and/or translates.

First drum housing (314) also comprises at least one drum post hole (330) operable to couple with at least one drum post (315) of second drum housing (318). As a result, first drum housing (314) and second drum housing (318) may be selectively coupled together such that rotation and translation of first drum housing (314) is operable to effectuate rotation and/or translation of second drum housing (318).

Figure 6:
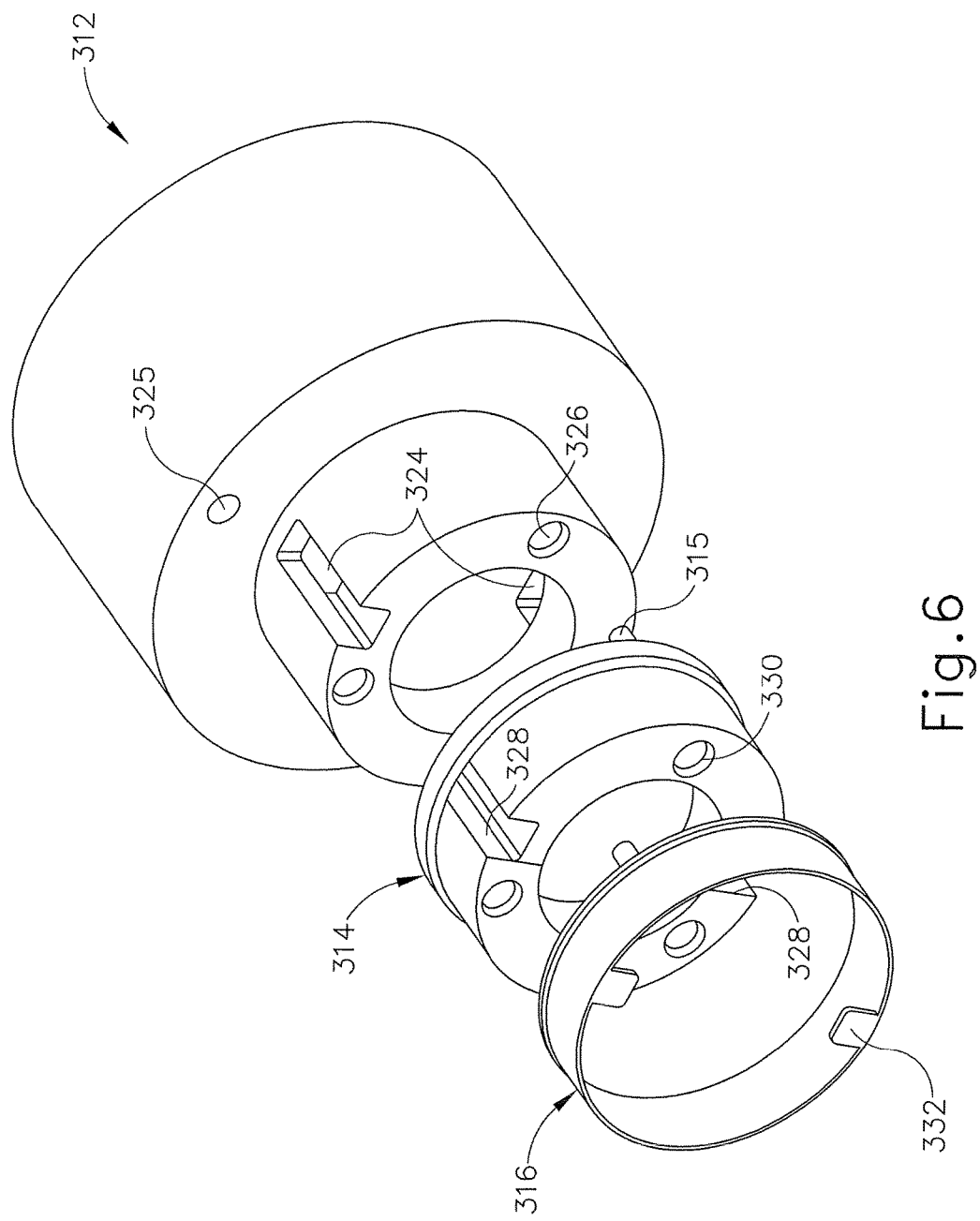
FIG. 6 depicts a perspective, exploded view of an exemplary nose cone, drum housing, and drum contact of the transducer carrier assembly of FIG. 5.

It will be appreciated that in the exemplary version, one or more wires may be routed along the length of transducer carrier assembly (300). FIG. 6 shows one exemplary path that such a wire(s) may travel. Nose cone (312) has a nose cone wire channel (324) formed within nose cone (312). Wire channel (324) comprises an elongated, rectangular channel positioned at the distal end of nose cone (312) where at least a portion of wire channel (324) extends through nose cone (312) such that a wire may be guided from the inside of nose cone (312) to the outside of nose cone (312) through wire channel (324). Furthermore, first drum housing (314) has a drum channel (328) formed therein. Drum channel (328) extends through the proximal end of drum channel (314), and as a result, a wire, which will be described in more detail below, may be routed through wire channel (324) and drum channel (328). Drum channel (328) has an elongated rectangular shape, but any suitable shape for drum channel (328) may be used as would be apparent to one of ordinary skill in the art in view of the teachings herein. In the present example, transducer carrier assembly (300) comprises drum channels (328) and wire channels (324) occurring as a pair of opposing drum channels (328) and a pair of opposing wire channels (324); however, any suitable number of drum channels (328) and wire channels (324) may be used as would be apparent to one of ordinary skill in the art in view of the teachings herein. Nose cone (312) further has at least one wire hole (325) through which a wire may be routed. As such, wires, or various other suitable components may be routed through wire hole (325) to wire channel (324) and then to drum channel (328). In other merely exemplary versions, wires or various other components may be routed through wire channel (324) directly, skipping wire hole (325).

FIG. 7 shows a cross sectional view of transducer carrier assembly (300) along with wires to show the path in which wires can travel along transducer carrier assembly (300). In particular, contact wires (334) and piezo wires (336) are shown traveling along the length of transducer carrier assembly (300). In the present example, a set of two contact wires (334) extend from first lead (334) and are routed along the outside of first cover (302) and second cover (304). Contact wires (334) then connect to first housing contact (323) and second housing contact (322). While the exemplary version comprises two contact wires (334) it will be appreciated that any suitable number of contact wires may be used as would be apparent to one of ordinary skill in the art in view of the teachings herein.

Piezo wires (336), conversely, travel entirely on the inside of first cover (302) and second cover (304). In some instances, it is contemplated that piezo wires (336) may travel partially within first cover (302) and second cover (304) rather than entirely within first cover (302) and second cover (304). As can be seen from the exemplary version, there are two piezo wires (336), but any suitable number of piezo wires (336) may be used as would be apparent to one of ordinary skill in the art in view of the teaching herein. In the exemplary version, piezo wires (336) extend from second lead (356) then pass underneath first cover (302) and second cover (304) as well as underneath nose cone (312). Piezo wires (336) then pass through wire hole (325) and travel along wire channel (324) to drum channel (328). One of piezo wires (336) then connects to first drum contact (316). The second of piezo wires (336) connects to second drum contact (320). Since first drum contact (316) and second drum contact (320) are in communication with first housing contact (323) and second housing contact (322), respectively, piezo wires (336) are in communication with contact wires (334). It will be appreciated that once such communication between piezo wires (336) and contact wires (334) is established, transducer carrier assembly (300) may be translated and/or rotated without breaking or interrupting the electrical communication between piezo wires (336) and contact wires (334).

Figure 8:
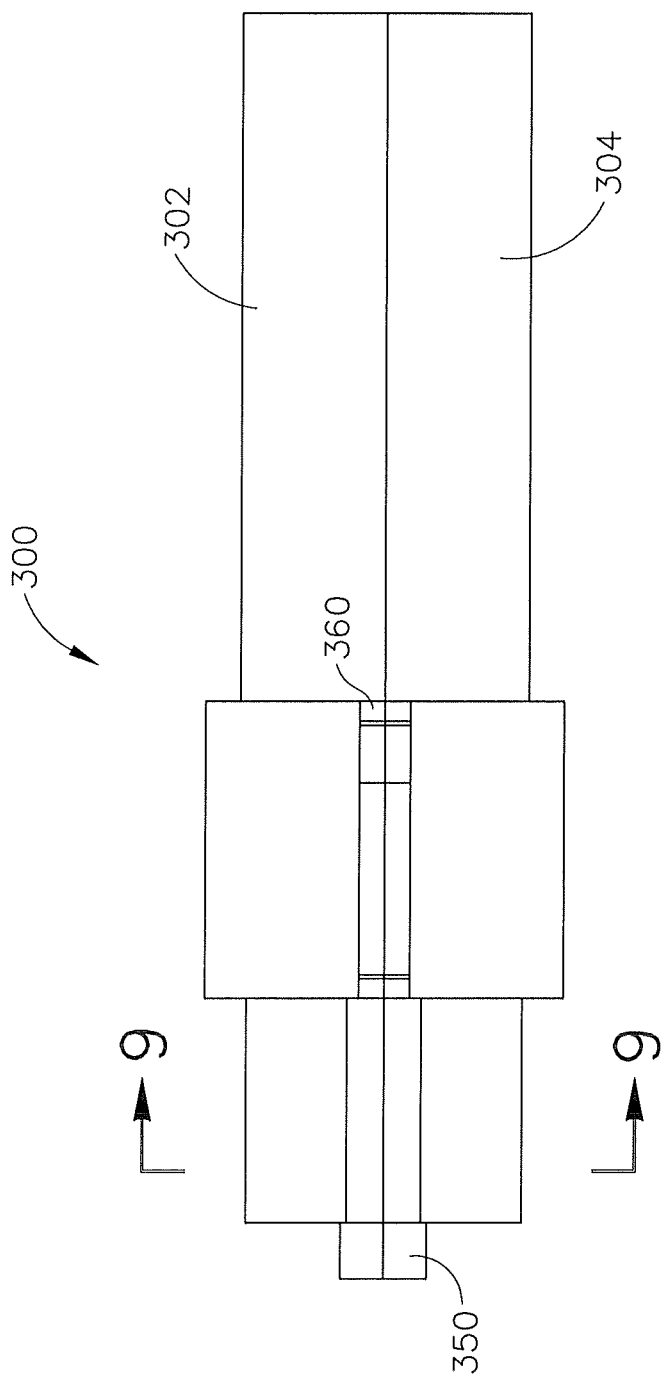
FIG. 8 depicts a side view of the transducer carrier assembly of FIG. 5.
Figure 10:
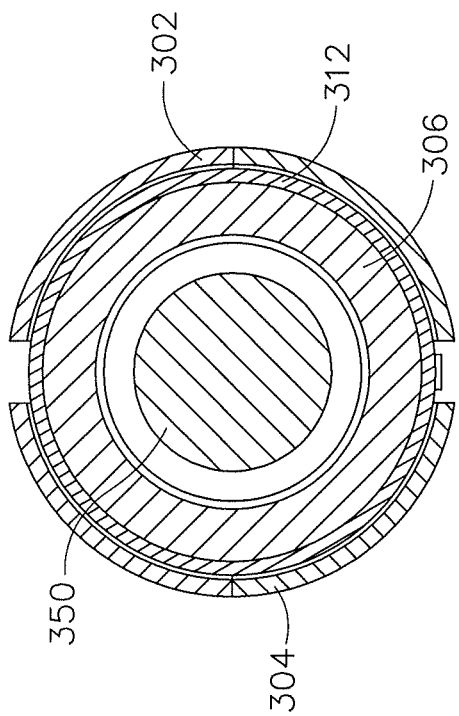
FIG. 10 depicts a cross sectional view of the transducer carrier assembly of FIG. 5 taken along line 10-10 of FIG. 7.
Figure 9:
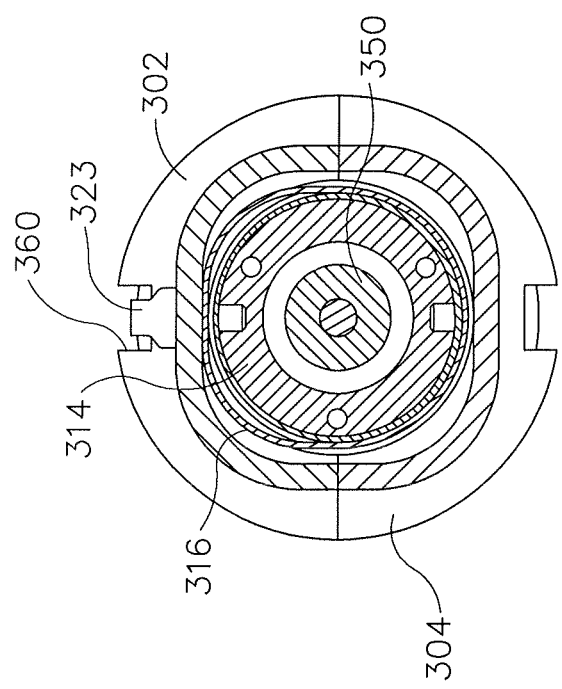
FIG. 9 depicts a cross sectional view of the transducer carrier assembly of FIG. 5 taken along line 9-9 of FIG. 8.
Figure 11:
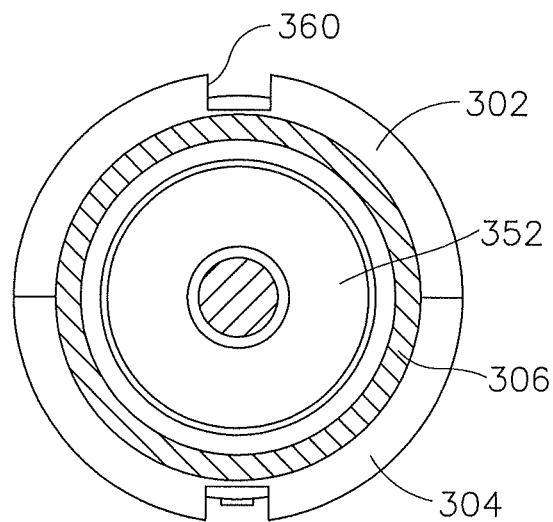
FIG. 11 depicts a cross sectional view of the transducer carrier assembly of FIG. 5 taken along line 11-11 of FIG. 7.

FIG. 8 shows transducer carrier assembly (300) with first cover (302) and second cover (304) closed together. FIGS. 9-11 show various cross sectional views of transducer carrier assembly (300). For instance, FIG. 9 shows a cross section of transducer carrier assembly (300) along line 9-9. FIG. 10 shows a cross section of transducer carrier assembly (300) along line 10-10. Furthermore, FIG. 11 shows a cross section of transducer carrier assembly (300) along line 11-11.

IV. Transducer Carrier Assembly with Coiled Wire

In some exemplary versions, it will be appreciated that transducer (100, 352) may be rotated or otherwise moved in a variety of ways before, during, or after operation of transducer. Furthermore, it will be appreciated that wires may be attached to transducer (100, 352) or otherwise in mechanical communication with transducer (100, 352) as may be the case with, for example, piezo wires (336) and contact wires (334). Finally, it will be appreciated that it may be desirable to construct such above referenced wires and/or any other wires and/or connecting mechanisms in such a way that facilitates such movement of transducer (100, 352) relative to such wires.

Figure 12:
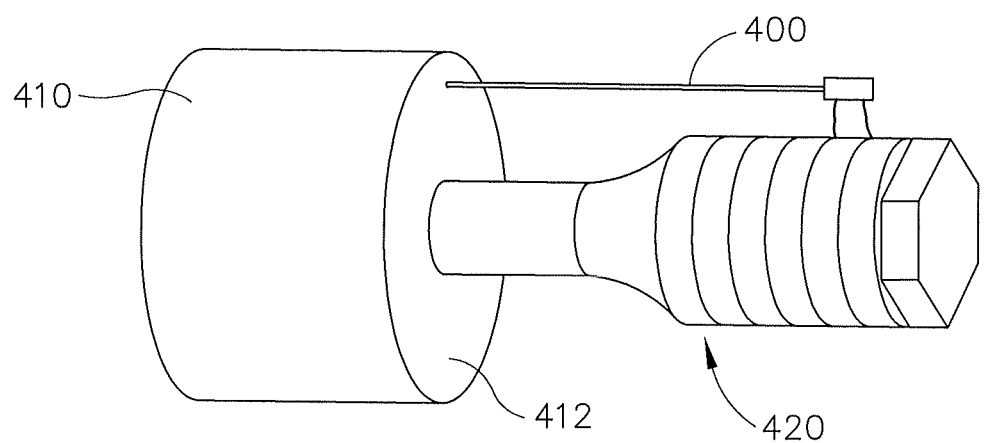
FIG. 12 depicts a side perspective view of an exemplary alternative version of a wire with a mounting ring and a transducer.

FIG. 12 shows an exemplary mounting ring (410) with a wire (400). In the present example, wire (400) provides electric communication between transducer (420) and a slip ring assembly, which is further in communication with a power source to activate transducer (420). By way of example only, such a slip ring assembly may be configured in accordance with the teachings above and/or in accordance with teachings of one or more references cited herein. Transducer (420) is inserted into a retention channel (412) of mounting ring (410), such that mounting ring (410) is operable to provide structural support to transducer (420) within a hand piece (e.g., within handle assembly (60) shown in FIG. 1). It will be understood that mounting ring (410) may remain fixed in handle assembly (60), whereas transducer (420) translates and/or rotates relative to handle assembly (60) and mounting ring (410). In some versions, mounting ring (410) rotates with transducer (420) relative to handle assembly (60); yet transducer (420) still translates relative to mounting ring (410). It should also be understood that various types of bearings may be interposed between mounting ring (410) and handle assembly (60) and/or between mounting ring (410) and transducer (420) to provide structural support while permitting rotation. Wire (400) is in communication with transducer (420) through a contact (414) and leads (416). However, any suitable method of establishing communication between wire (400) and transducer (420) may be used as would be apparent to one of ordinary skill in the art in view of the teachings herein.

Wire (400), in the exemplary version, comprises a self coiling wire such that when wire (400) is not under tension or is under a low amount of tension, wire (400) retracts or otherwise automatically coils itself, reducing its effective length. It will be appreciated that constructing wire (400) to be self coiling may allow wire (400) to be used in conjunction with transducer (420) without obstructing the use or rotation/translation of transducer (420). In other exemplary versions, rather than having a self-coiling construction, wire (400) may be constructed using an elastomeric conductive material such that rather than retracting using a coiling motion, wire (400) longitudinally shrinks by retracting along its own length in the absence of tension. Other suitable means for retracting wire (400) may be used as would be apparent to one of ordinary skill in the art in view of the teachings herein. In some versions as noted above, transducer (420) translates relative to mounting ring (410). Such translation will change the amount of length needed from wire (400). By reducing its own effective length in response to reduced tension, wire (400) may remain substantially straight as transducer (420) translates distally and proximally. In other words, wire (400) avoids going slack, and thereby avoids drooping into contact with transducer (420). Such avoidance of lateral contact with transducer (420) may reduce the likelihood that an activated transducer adversely impacts performance of wire (400) and/or that wire (400) adversely impacts performance of transducer (420). In addition or in the alternative, avoiding slackness/drooping in wire (400) may reduce the likelihood that wire (400) will get snagged on other components during rotation and/or translation of transducer (420).

V. Miscellaneous

It is contemplated that various teachings herein may be combined in numerous ways, and it should be understood that none of the teachings herein are intended to represent the limits of the inventors' contemplation. Various other examples of how several features of the surgical instruments described herein may be carried out in practice will be apparent to those of ordinary skill in the art in view of the teachings herein, and those examples are well within the inventors' contemplation.

By way of example only, at least a portion surgical device (100), active assembly (160), and/or other components referred to herein may be constructed in accordance with at least some of the teachings of U.S. Pat. No. 6,500,176 entitled "Electrosurgical Systems and Techniques for Sealing Tissue," published Dec. 31, 2002, the disclosure of which is incorporated by reference herein; U.S. Pat. No. 7,416,101 entitled "Motor-driven Surgical Cutting and Fastening Instrument with Loading Force Feedback," published Aug. 26, 2008, the disclosure of which is incorporated by reference herein; U.S. Pat. No. 7,738,971 entitled "Post-sterilization Programming of Surgical Instruments," published Jun. 15, 2010, the disclosure of which is incorporated by reference herein; U.S. Pub. No. 2006/0079874 entitled "Tissue Pad for Use with an Ultrasonic Surgical Instrument," published Oct. 7, 2005, the disclosure of which is incorporated by reference herein; U.S. Pub. No. 2007/0191713 entitled "Ultrasonic Device for Cutting and Coagulating," published Oct. 11, 2006, the disclosure of which is incorporated by reference herein; U.S. Pub. No. 2007/0282333 entitled "Ultrasonic Waveguide and Blade," published May 22, 2007, the disclosure of which is incorporated by reference herein; U.S. Pub. No. 2008/0200940 entitled "Ultrasonic Device for Cutting and Coagulating," published Jan. 15, 2008, the disclosure of which is incorporated by reference herein; U.S. Pub. No. 2009/0209990 entitled "Motorized Surgical Cutting and Fastening Instrument Having Handle Based Power Source," published Feb. 14, 2008, now U.S. Pat. No. 8,657,172, issued on Feb. 25, 2014, the disclosure of which is incorporated by reference herein; U.S. Pub. No. 2010/0069940 entitled "Ultrasonic Device for Fingertip Control," published Sep. 11, 2009, now U.S. Pat. No. 8,657,172, issued on May 5, 2015, the disclosure of which is incorporated by reference herein; U.S. Patent App. Publ. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the present invention have application in conventional endoscopic and open surgical instrumentation as well as application in robotic-assisted surgery. An exemplary robotic-assist surgery system is disclosed in U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
    (a) an ultrasonic transducer operable to deliver energy;
    (b) a body operable to support the ultrasonic transducer;
    (c) a shaft extending distally from the body, wherein the shaft defines a longitudinal axis;
    (d) a transducer carrier assembly, wherein the transducer carrier assembly is in communication with the body, wherein the ultrasonic transducer is contained within the transducer carrier assembly, wherein the ultrasonic transducer is operable to rotate relative to the transducer carrier assembly and about the longitudinal axis such that the transducer carrier assembly is configured to enable rotation of the ultrasonic transducer relative to the body, wherein the transducer carrier assembly is operable to translate relative to the body such that the transducer carrier assembly is configured to enable translation of the ultrasonic transducer relative to the body;
    and
    (e) an end effector at a distal end of the shaft, wherein the end effector includes an ultrasonic blade in acoustic communication with the ultrasonic transducer, wherein the shaft and the ultrasonic blade are configured to translate together relative to the body in response to translation of the ultrasonic transducer within the body, wherein the shaft and the ultrasonic blade are configured to rotate together relative to the body about the longitudinal axis in response to rotation of the ultrasonic transducer within the transducer carrier assembly.

2. The surgical instrument of claim 1, wherein the transducer carrier assembly comprises a first cover and a second cover, wherein the first cover is configured to couple with the second cover, wherein the first cover and the second cover are operable to fit over the ultrasonic transducer.

3. The surgical instrument of claim 2, wherein the first cover and the second cover are symmetrically shaped.

4. The surgical instrument of claim 1, wherein the transducer carrier assembly comprises a first drum housing and a second drum housing, wherein the surgical instrument further comprises a set of piezo wires and a set of contact wires, wherein the piezo wires are configured to provide electrical communication internal to the first drum housing and to the second drum housing, wherein the contact wires are configured to provide electrical communication external to the first drum housing and to the second drum housing.

5. The surgical instrument of claim 4, wherein the first drum housing is in communication with a first drum contact, and the second drum housing is in communication with a second drum contact.

6. The surgical instrument of claim 5, wherein the first drum contact comprises a slip ring contact, wherein the second drum contact comprises a slip ring contact.

7. The surgical instrument of claim 5, wherein the first drum contact is configured to encircle the first drum housing, wherein the second drum contact is configured to encircle the second drum housing.

8. The surgical instrument of claim 4, wherein the first drum housing and the second drum housing both comprise a cylindrical shape, wherein the first drum housing and the second drum housing are positioned in an end to end configuration.

9. The surgical instrument of claim 4, wherein the first drum housing and the second drum housing have an identical shape.

10. The surgical instrument of claim 1, wherein the transducer carrier assembly comprises a first drum housing and a second drum housing, wherein the first drum housing defines at least one opening, wherein the second drum housing comprises at least one post, wherein the first drum housing and the second drum housing are connected to each other by coupling the at least one opening and the at least one post.

11. The surgical instrument of claim 1, wherein the transducer carrier assembly comprises a nose cone, wherein the nose cone comprises a channel configured to guide a wire along at least a portion of the nose cone.

12. The surgical instrument of claim 1 wherein the transducer carrier assembly comprises a first drum housing and a second drum housing, wherein the first drum housing comprises a channel configured to guide a wire along at least a portion of the first drum housing.

13. The surgical instrument of claim 1, further comprising at least one set of wires extending along the length of the transducer carrier assembly, wherein the at least one set of wires is configured to be self coiling.

14. The surgical instrument of claim 1, further comprising at least one set of wires extending along the length of the transducer carrier assembly, wherein the at least one set of wires is configured to longitudinally retract in response to a reduction in tension.

15. A surgical instrument comprising:
(a) an ultrasonic transducer;
(b) a body;
(c) a transducer carrier assembly, wherein the transducer carrier assembly comprises a cover assembly, wherein the transducer carrier assembly is in communication with the body, wherein the transducer carrier assembly is in further communication with the ultrasonic transducer wherein the ultrasonic transducer is housed within the cover assembly, wherein the ultrasonic transducer is operable to rotate within the cover assembly such that the transducer carrier assembly is configured to enable rotation of the ultrasonic transducer relative to the body, wherein the transducer carrier assembly is further configured to enable translation of the ultrasonic transducer relative to the body;
(d) a shaft extending distally from the body, wherein the shaft defines a longitudinal axis; and
(e) an end effector at a distal end of the shaft, wherein the end effector has an ultrasonic blade in acoustic communication with the ultrasonic transducer, wherein the shaft and the ultrasonic blade are configured to translate together relative to the body in response to translation of the ultrasonic transducer relative to the body, wherein the shaft and the ultrasonic blade are configured to rotate together relative to the body and about the longitudinal axis of the shaft in response to rotation of the ultrasonic transducer relative to the cover assembly of the transducer carrier assembly and about the longitudinal axis of the shaft.

16. A surgical instrument comprising:
(a) an ultrasonic transducer;
(b) a body;
(c) a shaft extending distally from the body along a longitudinal axis; and
(d) a transducer carrier assembly, wherein the transducer carrier assembly is in communication with the body, wherein the ultrasonic transducer is supported by the transducer carrier assembly, wherein the ultrasonic transducer is confined within the transducer carrier assembly, wherein he transducer carrier assembly is configured to enable translation of the ultrasonic transducer relative to the body, wherein the transducer carrier assembly is further configured to enable rotation of the ultrasonic transducer relative to the transducer carrier assembly and the body about the longitudinal axis of the shaft;
and
(e) an end effector at a distal end of the shaft, wherein the shaft is configured to translate relative to the body in response to translation of the ultrasonic transducer relative to the body, wherein the end effector includes an ultrasonic blade in acoustic communication with the ultrasonic transducer, wherein the ultrasonic blade is configured to rotate relative to the body and about the longitudinal axis of the shaft when the ultrasonic transducer rotates about the longitudinal axis of the shaft and within the transducer carrier assembly.

* * * * *

UNITED STATES PATENT AND TRADEMARK OFFICE
CERTIFICATE OF CORRECTION

PATENT NO. : 9,763,690 B2  
APPLICATION NO. : 13/269875  
DATED : September 19, 2017  
INVENTOR(S) : Rupp et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 991 days.

Signed and Sealed this  
Sixth Day of February, 2018

Joseph Matal  
*Performing the Functions and Duties of the*  
*Under Secretary of Commerce for Intellectual Property and*  
*Director of the United States Patent and Trademark Office*